United States Patent [19]
Pappas et al.

[11] Patent Number: 4,932,974
[45] Date of Patent: Jun. 12, 1990

[54] PROSTHETIC DEVICE WITH PREDETERMINED CRYSTAL ORIENTATION

[76] Inventors: Michael J. Pappas, 61 Gould Pl., Caldwell, N.J. 07006; Frederick F. Buechel, 76 Crest Dr., South Orange, N.J. 07079

[21] Appl. No.: 377,910

[22] Filed: Jul. 6, 1989

[51] Int. Cl.$^5$ .......................................... A61F 00/000
[52] U.S. Cl. ................................................. 623/16
[58] Field of Search .................... 623/16, 18, 19, 20, 623/22, 23, 66, 907; 148/404; 164/35

[56] References Cited

U.S. PATENT DOCUMENTS

| | | | |
|---|---|---|---|
| 3,662,405 | 5/1972 | Bortz et al. | 623/16 |
| 3,677,835 | 7/1972 | Tieni et al. | 148/404 |
| 3,877,080 | 4/1975 | Olcott | 623/16 |
| 4,058,415 | 11/1977 | Walter | 623/16 |
| 4,122,605 | 10/1978 | Hirabayashi et al. | 623/16 |
| 4,518,442 | 5/1985 | Chin | 148/404 |
| 4,580,613 | 4/1986 | Miller et al. | 164/35 |
| 4,605,452 | 8/1986 | Gemma et al. | 148/404 |

FOREIGN PATENT DOCUMENTS

| | | |
|---|---|---|
| 22724 | 1/1981 | European Pat. Off. . |
| 2805868 | 8/1979 | Fed. Rep. of Germany . |
| 2948792 | 6/1980 | Fed. Rep. of Germany . |
| 2361093 | 3/1978 | France . |

OTHER PUBLICATIONS

"Casting and Properties of Unidirectionally-Solidified Superalloys", by M. Gell, C. P. Sullivan and F. L. Versnyder—pp. 1–35.

"The Development of Single Crystal Superalloy Turbine Blades", By M. Gell, D. N. Duhl and A. F. Giamei—Superalloys 1980—pp. 205–214.

"Monocrystaloys—A New Concept in Gas Turbine Materials-The Properties and Characteristics of PWA 1409", by B. J. Piearcey and F. L. VerSnyder—Feb. 2, 1966—pp. 1–28.

*Primary Examiner*—David J. Isabella
*Attorney, Agent, or Firm*—Anthony J. Casella; Gerald E. Hespos

[57] ABSTRACT

Prosthetic device such as bone plates, stem-type prostheses such as femoral or humeral prostheses, or intramedullary rods are substantially improved by utilizing casting techniques that provide columnar or monocrystalline grain structure, with the <001> crystal direction oriented substantially parallel to the neutral axis, thereby increasing flexibility of the prosthesis and increasing loading on the bone, whereby disuse-atrophy is reduced and bone healing is facilitated; similarly, the crystal direction may be oriented to increase the stiffness of the prosthesis to resist tension.

10 Claims, 3 Drawing Sheets

U.S. Patent   Jun. 12, 1990   Sheet 1 of 3   4,932,974
FIG. 1
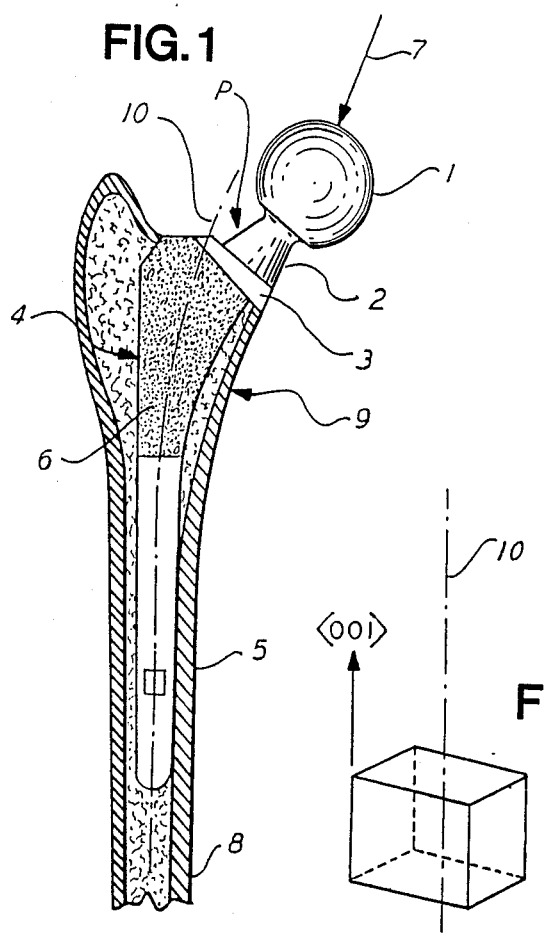
FIG. 2
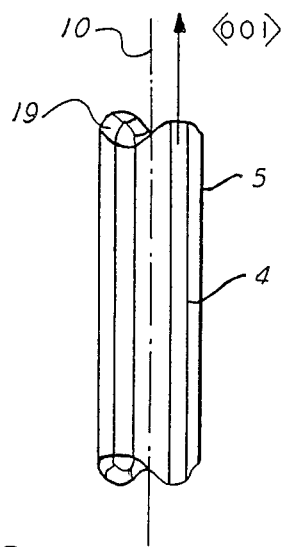
FIG. 1a
FIG. 3
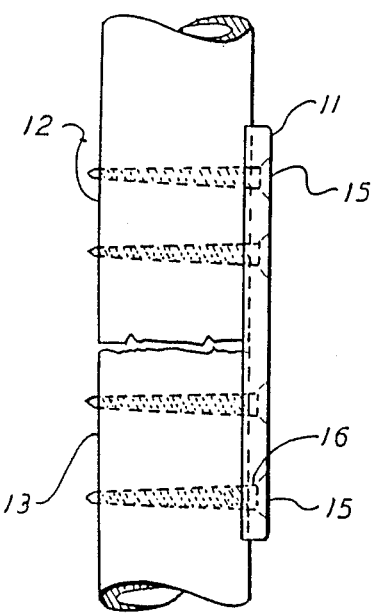
FIG. 4
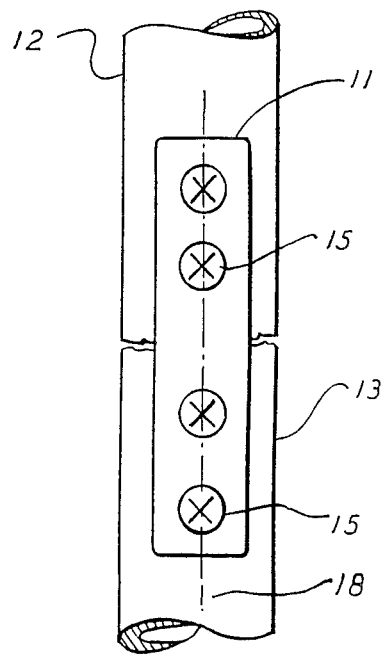

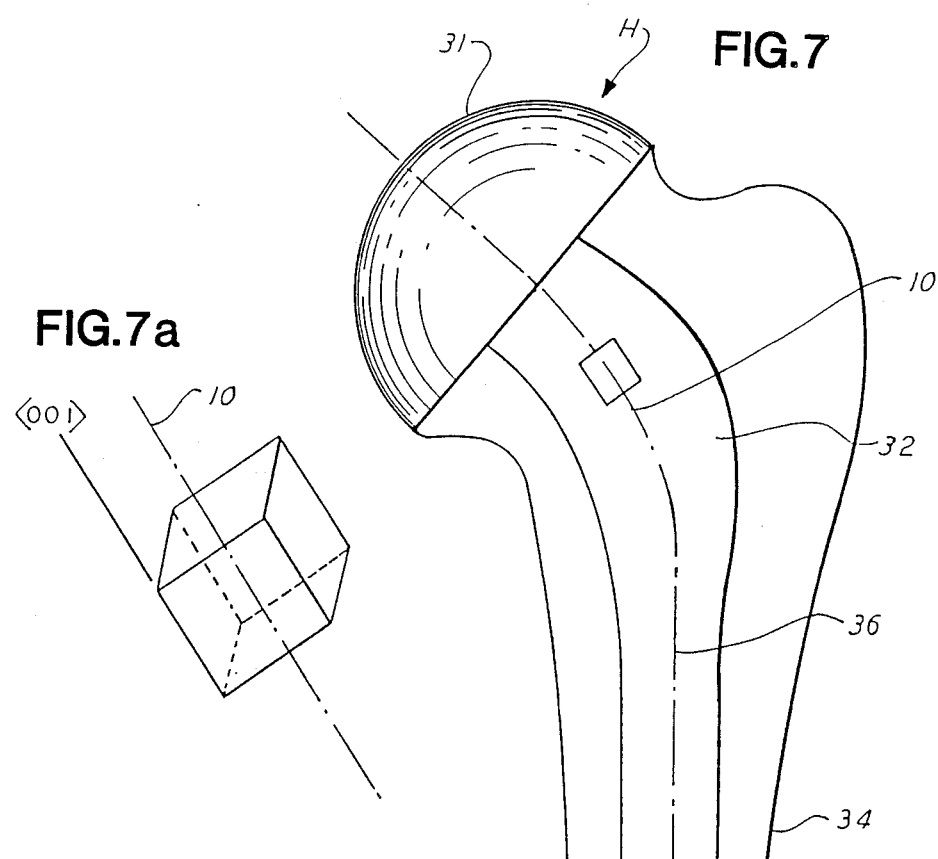
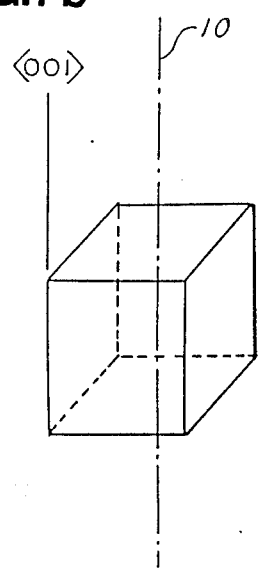
FIG. 7
FIG. 7a
FIG. 7b

PROSTHETIC DEVICE WITH PREDETERMINED CRYSTAL ORIENTATION

This application is a continuation of application Ser. No. 612,083 which was filed on May 21, 1984 now abandoned.

BACKGROUND OF THE INVENTION

Structural prosthetic devices such as bone plates, joint replacement stems such as femoral and shoulder stem type prostheses, and intramedullary rods are used to transmit loads between bones or bone segments. Such prostheses are subjected to bending, axial compression, and shear loads. Such bending loads usually produce moments applied about axes perpendicular to a neutral axis representing the locus of points through the centroids of cross-sections of the prostheses taken normal to the neutral axis which is generally along the length of the prosthetic device. Torsion is often also applied about the neutral axis.

Since structural prosthetic devices are generally made of metal which is relatively rigid compared to bone, these devices frequently transfer load between bones or bony segments in a manner which greatly reduces loading on the bone in certain regions thereby inhibiting proper healing of the bone. It is a known property of bone that bone must be subjected to loading or disuse-atrophy will occur. Such protection of the bone, typically called stress shielding, frequently results in disuse-atrophy of certain regions of the bone providing an unhealthy situation for fixation of joint replacement prostheses of fracture fixation prostheses. This is particularly true where metallic fracture fixation prostheses must be removed, as is now recommended by some experts in the field, to avoid release of metal corrosion products into the body. Such removal will eliminate the structural contribution of the metallic fixation prostheses leaving only weakened bone to resist loading and such removal produce fracture of the bone unless healthy healing has occured. It is often, therefore, desirable to limit the stiffness of structural prostheses against certain loading modes so that at least after initial healing, preferably, as much of the load as possible is transmitted between bone or bony segments by the bone or bony segments themselves and that the prostheses simply act to align the segments and connect the prostheses to bone.

Further, where fixation plates are used to align fractured or resected bone segments the stiffness of the plate can inhibit bone growth between bone segments. Thus, bending flexibility is desired in order to increase the load transmitted between segments thereby stimulating bone growth.

Several investigators have been experimenting with plastic and composite plates in order to minimize the excessive stiffness of structural prostheses. While the development of such composite of plastic structural prostheses has much potential, the body is a hostile enviornment and plastics and composites frequently are severely affected by aging and exposure to the enviroment within the body. Further, there is limited knowledge about how plastics and composites capable of supporting the needed loads would behave in the body over long periods of time and what the effects of the corrosion products resulting from exposure of these materials to body fluids under the action of stresses would be. The bio-compatibility or the ability of the body to tolerate such plastics is not well understood. Conversely, metals (in particular cobalt chromium and titanium alloys) have been used in the body for several decades and they are found to be fatigue resistant, relatively corrosion resistant, and well tolerated by the body. Thus, it is advantageous to use these materials at least until such time as plastics and composites are proven to be effective in such use.

A principal advantage titanium and its alloys for use in femoral stems arises from the fact that these alloys are substantially less rigid than cobalt-chromium or other alloys used in this application. This increased flexibility results in lower stem loading, reducing stem stresses, and higher loading of the bone, reducing disuse-atrophy. Unfortunately, the notch sensitivity of surgical titanium alloy and the attendant drastic reduction in fatigue strength resulting from the use of a metallic porous surface on this material appears to limit the usefulness of porous coated titanium alloys. Thus, titanium alloys may not be well adapted for the exploitation of the substantial benefits available from the use of such coatings for both cement and biological fixation, but is a material of choice where such coatings are not used. On the other hand, cobalt chromium alloys do not appear to be notch sensitive, and seem well adapted for such exploitation.

The stiffness of structural prosthetic devices or fixation prostheses can, of course, be affected by the design of the prostheses itself. However, strength and geometric requirements (for example the need for a femoral stem to fit adequately into a femoral intramedullary canal) often limit the ability to provide as flexible a structural prosthesis as one would like. The use of more flexible metals such as titanium is also advantageous in this application since they can produce additional prosthesis flexibility. However, even with the use of titanium there are instances where a still more flexible metallic material would be preferred. Furthermore, many orthopaedic surgeons prefer to use cobalt chromium alloys since there is much more experience with the use of these alloys in the body than there is with titanium. Thus, there is a further need in the structural prosthetic device art for bio-compatible materials, in particular metals, of increased flexibility.

In some instances such as the use of bone plates for fracture fixation, increased bending and axial flexibility are desirable but increased torsional flexibility is undersirable since torsional stiffness helps resist movement between bone segments thereby stabilizing the fracture and thus promoting healing.

It has been discovered that single crystal materials developed for use a turbine blades in jet engines offer the potential for providing such increased flexibility in preferred directions while simultaneously providing increase stiffness in other preferred directons. The manufacture of parts using these alloys is described in a chapter entitled "The Development of Single Crystal Superalloy Turbine Blades" by M. Gell et al. in a book entitled "Superalloys 1980" which is a publication of the Proceedings of the Fourth International Symposium on Superalloys published in 1980; the article is found on pages 205-215 of the book which is published by The American Society for Metals. Crystals are anisotropic with respect to material properties. Stiffness and strength depend on direction. Cubic crystals, for example, have substantially lower stiffness in the $<001>$ direction. Metals conventionally used for structural or fixation prostheses are polycrystalline in nature and generally have equiaxed grains. Such materials exhibit isotropic properties since the grain and crystal orientations are random and the stiffness is thus intermediate in value between the minimum and maximum crystal stiffness values.

Analogous technology to the single crystal materials is the development of directionally solidified materials or polycrystalline columnar grain structure. Such directionally solidified alloys are discussed in an article by Francis L. VerSnyder and N.E. Shank entitled "The development of Polymer Grain in Single Crystal High Temperature Metals Through Directional Solidification" appearing in Material Sicence and Engineering, Vol.6, No.4, 1970, pp. 213–247; such alloys are also discussed in U.S. Pat. No. 3,677,835 noted above.

SUMMARY OF THE INVENTION

The invention generally relates to use of metallic structural prosthetic devices in which the crystalline structure of the metal is organized and oriented such that the flexibility and/or stiffness of the material is greater in certain preferred directions compared to conventional polycrystalline materials commonly used in the prosthetic art; appropriately used, the flexibility increases the rate of the bone regeneration thereby facilitating bone or bone segment healing with an attendant reduction in bone disuse-atrophy, and appropriately used, the stiffness provides increased bone segment stabilization thereby facilitation bone segment healing.

DESCRIPTION OF THE DRAWINGS

FIG. 1 is a diagrammatic side view, generally in cross-section, of a stem-type femoral prosthesis embodying the present invention and shown fixtured in the proximal end of a femur;

FIG. 1a is a diagrammatical illustration of cubic crystal structure of a single crystal material with a crystal direction having a preferred orientation in the $<001>$ crystal direction;

FIG. 2 is a diagrammatic illustration of polycrystalline columnar grain structure consisting of grain columns having a crystal direction with a preferred orientation in the $<001>$ direction.

FIGS 3 and 4 are, respectively, side and front elevational views of a fracture fixation or bone plate embodying the present invention and shown fixtured to bone or bony segments;

FIG. 7 is a diagrammatical side view of a stem-type humeral prosthesis embodying the present invention and shown fixtured in the proximal end of a humerus;

FIGS. 7a and 7b are views similar to FIG. 1a illustrating preferred crystal dirction orientation.

DESCRIPTION OF THE PREFERRED EMBODIMENTS

Figure 5:
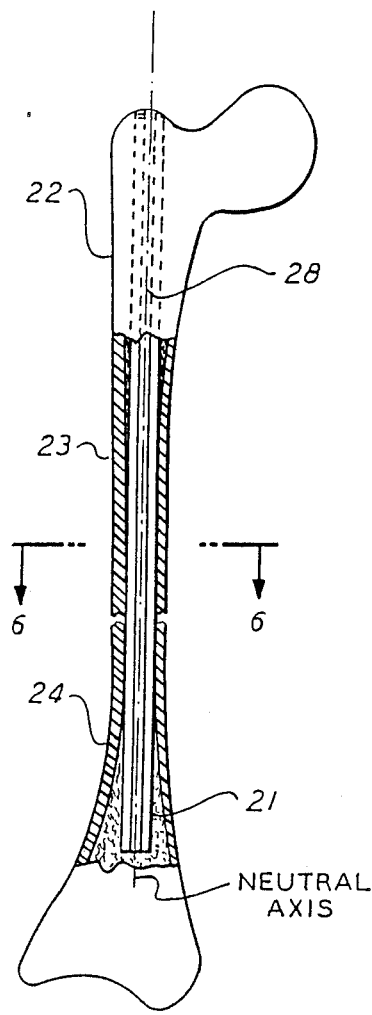
FIG. 5 is a diagrammatical illustration of an intramedullary fixation rod inserted into bone or bony segments for maintaining the segments in alignment and for facilitating bone healing.

Five embodiments of the invention are shown in the FIGS. FIG. 1 shows an embodiment of a stem-type femoral prosthesis P having a head 1, a neck 2, a collar 3 and a stem 4. The stem 4 is fixtured in the intramedullary cavity of a femur 5 along the outside surface of the stem by either the use of acrylic cement or by direct bone-ingrowth or biological fixation into a porous coating 6 on stem 4. The stem 4 transmits an applied load 7 from the acetabulum (not shown) to the shaft 8 of femur 5. Load 7 results in the axial compression shear and bending of the prosthesis P and femur 5 to which it is attached. Stem 4 and femur 5 act as a composite structure both sharing these applied loads. The proportion of loading shared by each structure is dependent on the relative stiffnesses of the structures with the stiffer structure generally carrying the greater portion of the applied shared load. It is desirable to prevent disuse-atrophy of the femur 5 by allowing the femur rather than the stem 4 to take most of the load. However, in conventional stem materials, particularly relatively rigid alloys such as cobalt chromium alloy, the stem carries the bulk of the applied shared load in the region of the proximal femur as indicated generally by region 9 thus often producing disuse-atrophy and resorption of the femur in this region.

In the invention, the femoral stem-type prosthesis P and in particular the stem 4 is made of a single crystal material or metal of cubic crystal structure wherein the $<001>$ crystal direction has an orientation generally along or parallel to the direction of a neutral axis 10. Alternately, the stem 4 could be cast with a polycrystalline columnar grain structure as shown in FIG. 1b consisting of grain columns 19 with a crystal orientation where the $<001>$ direction is parallel to the stem neutral axis 10. Under the loading conditions shown in FIG. 1, the stem 4 and femur 5 act as a beam-column. In such a loading condition, the principal strain directions in the stem are essentially parallel to the neutral axis. Thus, for example, where a stem is formed of a single crystal with the $<001>$ crystal direction substantially parallel to the neutral axis 10, such stem is significantly less stiff under the action of normally applied loads than an equiaxed conventional stem of the same material. With respect to bending and compression, a single crystal material stem of the construction described (e.g. single crystal cobalt chromium alloy) would possess for practial purposes a tensile modulus approximately equal to 18 million psi as compared to a tensile modulus of about 30 million psi for equiaxed grain material. (The application of single crystal technology to the manufacture of titanium stems in order to increase flexibility may also be utilized to improve the flexibility of titanium and other metallic stems.) As a result of this increased flexibility, the bone in region 9 (FIG. 1) will experience greater loading thereby reducing disuse-atrophy and resorption and thereby promoting bone healing and providing a healthier condition for maintenance of satisfactory bone stock in order to maintain fixation of the structural prosthesis, e.g. stem 4.

A second embodiment of the invention is shown in FIGS. 3 and 4 wherein the embodiment is a fracture fixation or bone plate 11. Such a plate is used to hold together bone or bony segments 12 and 13 so that these segments may be aligned during the bone healing process. The bone plate 11 is generally held to the bony segments 12 and 13 by the use of four or more screws 15 screwed into the bony segments through holes 16 in the plate. This plate is subjected to loading conditions similar to that of the femoral stem-type prosthesis discussed earlier, namely this loading includes axial compression, bending and torsion. Here again, if the plate 11 is made of single crystal material so that the <001> crystal orientation is directed along a neutral axis 18, the flexibility of the plate 11 with respect to the axial compression which is generally directed parallel to the neutral axis 18, bending moments which are generally acting about an axis perpendicular to the neutral axis and torsion which supplies the twisting moment generally parallel to the neutral axis, then the bone plate 11 will be more flexible in response to the bending and axial compression action on this shared applied loading than would be a bone plate made of equiaxed polycrystalline grains of a similar material as is the conventional practice. The bone plate 11, as the stem 4 of FIG. 1, could be cast with the columnar grain structure and crystal orientation of FIG. 7. It should be noted that the plate 11 is also stiffer in torsion than an equiaxed polycrystalline material since the crystal is stiffer in directions <111> and <101> which are associated with shear deformation. This increased stiffening effect is greater for a single crystal than for directionally solidified columnar grains.

Figure 6:
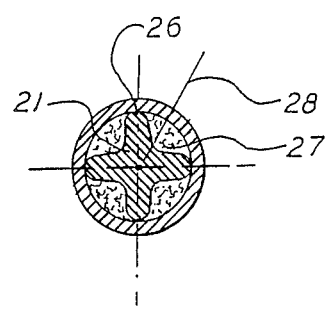
FIG. 6 is a cross-sectional view taken generally along the cross-sectional line 6—6 of FIG. 5.

The third embodiment is shown in FIGS. 5 and 6. This embodiment is an intramedullary fixation rod 21 shown inserted into the intramedulary cavity of a bone such as the femur 22 in order to hold bony segments 23 and 24 in alignment during the bone healing process. Intramedullary rod 21 is typically fluted on its outside surface as shown in FIG. 6 having projections 26 and depressions 27 providing twisting resistance between the rod and bone about the neutral axis 28 of the rod. This rod is subject to forces similar to those described in regard to the bone plate 11 (FIGS. 3 and 4) except that in the case of the rod 21 smoothness of its outer surface allows only minor transfer of compressive load along the rod and thus loading is dominated primarily by bending and torsion. In accordance with the teachings of the present invention, if the rod 21 is made of material, e.g. single crystal or columnar grain structure, such that crystalline orientation of the <001> direction of the material is made parallel to the neutral axis 28 of the rod 21, then the rod will be made more flexible with respect to bending and stiffer in torsion than a similar rod of the same material but of conventional equiaxed polycrystalline orientation material.

The fourth shown invention embodiment is a stem-type humeral prosthesis H of FIG. 7 having a head 31 and a stem 32 fixtured in the proximal end of a humerus 34. The stem 32 has a neutral axis 36 and the stem 32, in accordance with the teachings of the present invention and as set forth above with regard to the femoral stem-type prosthesis P of FIG. 1 may be made of single crystal or polycrystalline columnar grain structure having a crystal orientation where the <001> direction is parallel to the neutral axis 36 as illustrated by the cubes of FIGS. 7 A and 7 B. Such crystal direction orientation provides the same benefits with regard to reduction in bone disues-atrophy and facilitation of bone healing as taught above with regard to the femoral prosthesis P of FIG. 1.

Figure 8:
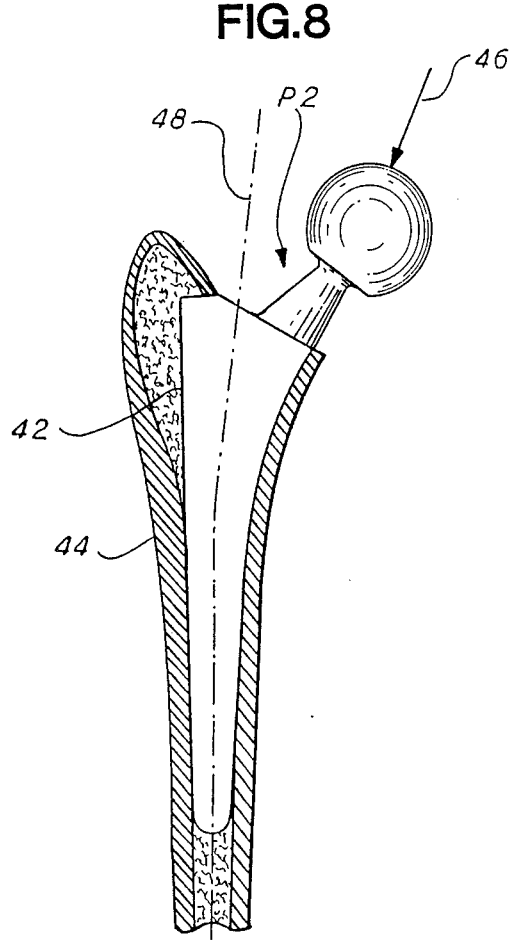
FIG. 8 is a diagrammatic side view, generally in cross-section, of a press-fit stem-type femoral prosthesis embodying the present invention and shown fixtured in the proximal end of a femur.

The fifth invention embodiment is a press-fit stem-type prosthesis such as the press-fit stem-type femoral prosthesis P2 illustrated in FIG. 8. The need for increased stem flexibility is particularly great for press- fit stem-type prostheses. The stem 42 of the prosthesis P2, as known to those skilled in the art, is made relatively thick as compared to conventional stems such as the stem 4 of the prosthesis P of FIG. 1 in order to fit tightly within the intramedullary canal of the proximal femur 44. With such a press-fit type stem, the shared load 46 is transmitted primarily by a wedging type contact similar to a tapered plug wedged into a tapered hole. The relatively large thickness or cross-sectional size of such stems results in a much stiffer stem than the noted conventional stems. Thus, press-fit type stems may increase stress shielding and its attendant disuse-atrophy. Thus, it will be understood that in accordance with the further teachings of this invention, a thicker stem 42 of a single crystal or of directionally solidified material having the crystal direction orientations illustrated in FIGS. 1a and 2 with respect to the neutral axis 48 (FIG. 8) will be provided with increased flexibility and attendant reduction in bone disuse-atrophy and enhance bone healing, as taught above. Such increased flexibility is of particularly great value with such thicker press-fit type stems.

It will be understood that the present invention is equally applicable to other stem-type structural prostheses such as, for example, finger, toe, wrist and tibial prostheses.

It will be further understood by those skilled in the art that many modifications and variations may be made in the present invention without departing from the spirit and the scope thereof.

What is claimed is:

1. A metallic prosthetic device having an elongated stem for fixation in an elongated portion of a first bone needing healing and load bearing means extending from said stem for mounting said prosthetic device to a second bone such that upon fixation of said stem in said elongated portion of said first bone, said stem and said first bone are subject to respective portions of a shared load applied thereto through said load bearing means, said stem of said prosthetic device consisiting entirely of a polycrystalline columnar grain metallic structure consisting of grain columns formed from metal having at least one predetermined crystal direction which is oriented generally parallel to the direction of elongation of the stem to provide said stem with an increase in flexibility in the direction of elongation of the first bone upon said fixation and in response to loads applied to said load bearing means, such that upon said fixation of said stem in said first bone, said increase in flexibility causes a decrease in the portion of the load carried by the stem and an increase in the portion of the load carried by the elongated portion of the first bone, to facilitate healing of the first bone by reducing bone disuse atrophy.

2. A prosthetic device as in claim 1 wherein said load bearing means comprises a substantially spherical head for mounting to said second bone.

3. A prosthetic device as in claim 1 wherein said load bearing means comprises an elongated neck extending from and angularly aligned to said elongated stem.

4. A metallic prosthetic device having an elongated stem for fixation in an elongated portion of a first bone needing healing and load bearing means extending from said stem for mounting said prosthetic device to a second bone such that upon fixation of said stem in said elongated portion of said first bone, said stem and said first bone are subject to respective portions of a shared load applied thereto through said load bearing means, said stem of said prosthetic device consisting entirely of a single crystal formed from metal having at least one predetermined crystal direction which is oriented generally parallel to the direction of elongation of the stem to provide said stem with an increase in flexibility in the direction of elongation of the first bone upon said fixation and in response to loads applied to said load bearing means, such that upon said fixation of said stem in said first bone, said increase in flexibility causes a decrease in the portion of the load carried by the stem and an increase in the portion of the load carried by the elongated portion of the first bone, to facilitate healing of the first bone by reducing bone disuse atrophy.

5. A prosthetic device as in claim 4 wherein said load bearing means comprises a substantially spherical head for mounting to said second bone.

6. A prosthetic device as in claim 4 wherein said load bearing means comprises an elongated neck extending from and angularly aligned to said elongated stem.

7. A prosthetic device as in claim 1 wherein the stem of the prosthetic device is formed a cobalt chromium alloy.

8. A prosthetic device as in claim 1 wherein the stem of the prosthetic device is formed metal comprising titanium.

9. A prosthetic device as in claim 4 wherein the stem of the prosthetic device is formed from a cobalt chromium alloy.

10. A prosthetic device as in claim 4 wherein the stem of the prosthetic device is formed from metal comprising titanium.

* * * * *